United States Patent
Mortier et al.

(10) Patent No.: US 11,069,136 B2
(45) Date of Patent: Jul. 20, 2021

(54) PRE-OPERATIVE SIMULATION OF TRANS-CATHETER VALVE IMPLANTATION

(71) Applicant: FEops NV, Ghent (BE)

(72) Inventors: Peter Mortier, Anzegem (BE); Gianluca De Santis, Ghent (BE)

(73) Assignee: FEops NV, Ghent (BE)

( * ) Notice: Subject to any disclaimer, the term of this patent is extended or adjusted under 35 U.S.C. 154(b) by 0 days.

(21) Appl. No.: 16/987,794

(22) Filed: Aug. 7, 2020

(65) Prior Publication Data
US 2020/0364936 A1 Nov. 19, 2020

Related U.S. Application Data

(63) Continuation of application No. 14/399,781, filed as application No. PCT/EP2013/058392 on Apr. 23, 2013, now Pat. No. 10,789,772.

(30) Foreign Application Priority Data

May 16, 2012 (WO) ................. PCT/EP2012/059207
Mar. 4, 2013 (WO) ................. PCT/EP2013/054276

(51) Int. Cl.
*G06T 17/20* (2006.01)
*A61B 34/10* (2016.01)
*A61B 17/00* (2006.01)
*A61F 2/24* (2006.01)

(52) U.S. Cl.
CPC ............. *G06T 17/20* (2013.01); *A61B 34/10* (2016.02); *A61B 2017/00783* (2013.01); *A61B 2034/102* (2016.02); *A61B 2034/104* (2016.02); *A61B 2034/105* (2016.02); *A61B 2034/108* (2016.02); *A61F 2/2415* (2013.01); *A61F 2/2496* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 8,315,812 B2 * | 11/2012 | Taylor | A61B 8/04 702/19 |
| 8,682,626 B2 | 3/2014 | Ionasec et al. | |
| 10,789,772 B2 | 9/2020 | Mortier et al. | |
| 2005/0043609 A1 | 2/2005 | Murphy et al. | |
| 2007/0135707 A1 | 6/2007 | Redel et al. | |
| 2011/0153286 A1 | 6/2011 | Zaeuner et al. | |
| 2015/0051884 A1 | 2/2015 | Grady et al. | |
| 2015/0112659 A1 | 4/2015 | Mortier | |
| 2016/0166332 A1 | 6/2016 | Wang et al. | |
| 2018/0289422 A1 | 10/2018 | Mortier et al. | |
| 2019/0357981 A1 | 11/2019 | Mortier et al. | |

FOREIGN PATENT DOCUMENTS

| | | |
|---|---|---|
| DE | 102012205504 A1 | 10/2013 |
| WO | WO 2013/156546 A2 | 10/2013 |
| WO | WO 2013/171039 A1 | 11/2013 |
| WO | WO 2014/009294 A1 | 1/2014 |
| WO | WO-2016038169 A1 | 3/2016 |
| WO | WO-2016/177647 A1 | 11/2016 |
| WO | WO-2018/141927 A1 | 8/2018 |
| WO | WO-2019/179793 A1 | 9/2019 |

OTHER PUBLICATIONS

Morlacchi et al. (Journal of Biomechanical Engineering (2011) vol. 133:11 pages.*
Antiga, et al., An image-based modeling framework for patient-specific computational hemodynamics, *Med. Biol. Eng. Comput.*, 46:1097-1112 (2008).
Auricchio, et al., Carotid artery stenting simulation: From patient-specific images to finite element analysis, *Medical Engineering & Physics*, 33:281-289 (2011).
Capelli, et al., Patient-specific simulations of transcatheter aortic valve stent implantation, *Med. Biol. Eng. Comput.*, 50:183-192 (2012).
De Santis, et al., Patient-specific computational fluid dynamics: structured mesh generation from coronary angiography, *Med. Biol. Eng. Comput*, 48:371-380 (2010).
Grbic, et al., Complete Valvular Heart Apparatus Model From 4D Cardiac CT, *Medical Image Analysis*, 16(5):1003-1014 (2012).
Lenoir, et al., Physics-Based Models for Catheter, Guidewire and Stent Simulation, *Medicine Meets Virtual Reality*, 14:305-310 (2006).
Morganti, et al., Simulation of transcatheter aortic valve implantation through patient-specific finite element analysis: Two clinical cases, *Journal of Biomechanics*, 47:2547-2555 (2014).
Mortier, et al., A Novel Simulation Strategy for Stent Insertion and Deployment in Curved Coronary Bifurcations: Comparison of Three Drug-Eluting Stents, *Annals. Of Biomedical Engineering*, 38(1):88-99 (2010)
Rocatello, et al., Patient-Specific Computer Simulation to Elucidate the Role of Contact Pressure in the Development of New Conduction Abnormalities After Catheter-Based Implantation of a Self-Expanding Aortic Valve, *Cir. Cardiovasc. Interv.*, pp. 1-9 (2018). .

(Continued)

*Primary Examiner* — Lori A. Clow
(74) *Attorney, Agent, or Firm* — Eversheds Sutherland (US) LLP; Christopher C. Bolten; Nicola A. Pisano

(57) ABSTRACT

In a first aspect, the present invention relates to a method for patient-specific virtual percutaneous implantation, comprising estimating a patient-specific anatomical model of a patient-specific aorta based on cardiovascular 2D or 3D medical image data and virtually deploying an implant model representing an implant into said patient-specific anatomical model. In a second aspect, the present invention provides a method for patient-specific virtual percutaneous implantation. In a third aspect, the present invention provides an implant for virtual percutaneous implantation. In a fourth aspect, the present invention provides a system for virtual percutaneous implantation.

30 Claims, 8 Drawing Sheets

(56) References Cited

OTHER PUBLICATIONS

Russ, et al., Simulation of Transcatheter Aortic Valve Implantation under Consideration of Leaflet Calcification, *35th Annual International Conference of the IEEE EMBS,* Osaka, Japan, pp. 1-4 (2013).
Schneider et al., Modeling Mitral Valve Leaflets from Three-Dimensional Ultrasound, *Functional Imaging and Modeling of the Heart, Lecture Notes in Computer Science,* 6666:215-222 (2011).
Sun, et al., Simulated elliptical bioprosthetic valve deformation: Implications for asymmetric transcatheter valve deployment, *Journal of Biomechanics,* 43:3085-3090 (2010).
Viscardi, et al., Comparative Finite Element Model Analysis of Ascending Aortic Flow in Bicuspid and Tricuspid Aortic Valve, *Artificial Organs,* 34:1114-1120 (2010).
Vy, et al., Review of patient-specific simulations of transcatheter aortic valve implantation, *International Journal of Advances in Engineering Sciences and Applied Mathematics,* 8(1):2-21 (2016).
Wang, et al., Patient-specific Modeling of Biomechanical Interaction in Transcatheter Aortic Valve Deployment, *J. Biomech.,* 45(11):1965-1971 (2012).
Basri, et al., The Hemodynamic Effects of Paravalvular Leakage Using Fluid Structure Interaction; Transcatheter Aortic Valve Implantation Patient, Journal of Medical Imaging and Health Informatics, 6(5):1513-1518 (2016).
European Search Report dated Jul. 11, 2017 in EP Patent Appl. Serial No. 17154648.4.
International Search report and written opinion dated Jul. 30, 2013 in Int'l PCT Patent Application Serial No. PCT/EP2013/058392.
International Search report and written opinion dated Jun. 4, 2018 in Int'l PCT Patent Application Serial No. PCT/EP2018/052701.
Ghadimi, M.D., et al., Perioperative Conduction Disturbances After Transcatheter Aortic Valve Replacement, Journal of Cardiothoracic and Vascular Anesthesia, 27(6):1414-1420 (Dec. 2013).
Steinberg, Cardiac Conduction System Disease After Transcatheter Aortic Valve Replacement, American Heart Journal, 164(5):664-671 (Nov. 2012).
Sirois, et al., *Hemodynamic Impact of Transcatheter Aortic Valve Deployment Configuration,* Journal of Medical Devices, 7(4):040922. 1-040922.2 (Dec. 2013).

* cited by examiner

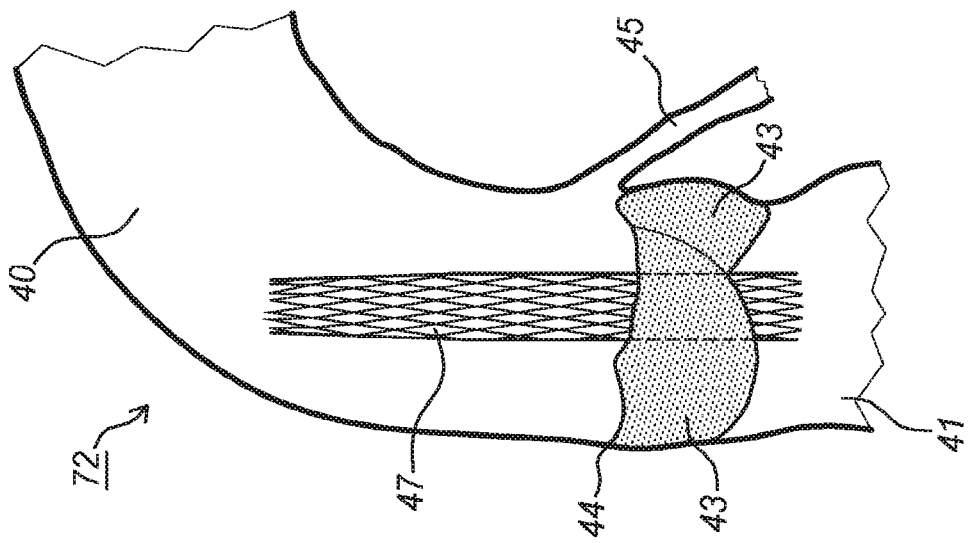
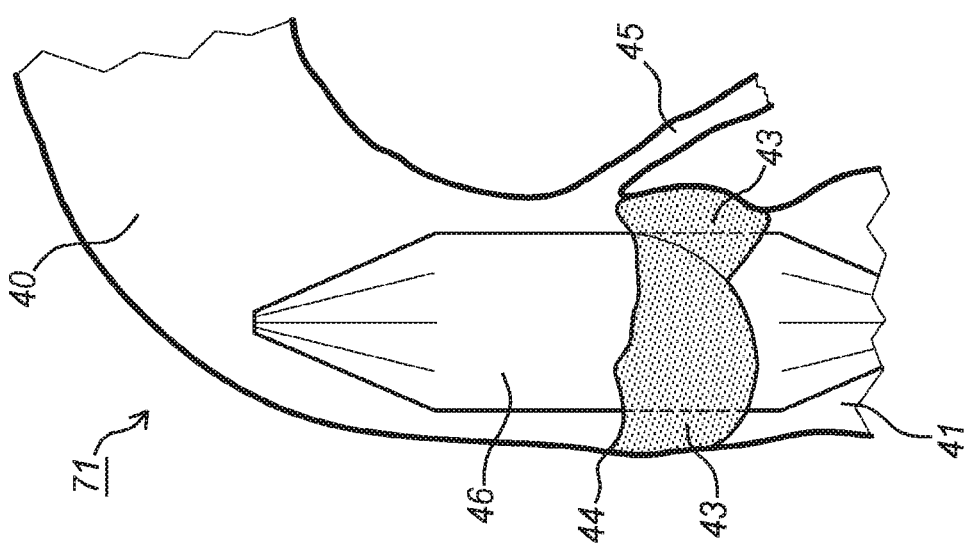
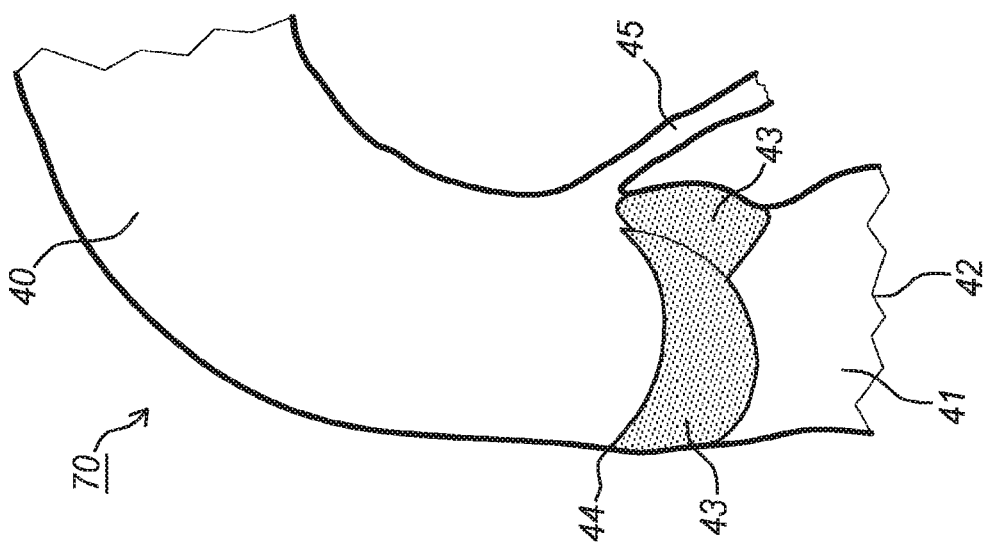
Fig. 4

PRE-OPERATIVE SIMULATION OF TRANS-CATHETER VALVE IMPLANTATION

CROSS-REFERENCE TO RELATED APPLICATIONS

This application is a continuation of U.S. patent application Ser. No. 14/399,781, filed Nov. 7, 2014, which is a national phase application under 35 U.S.C. § 371 of PCT/EP2013/058392, filed Apr. 23, 2013, which claims priority to International PCT Patent Application Serial No. PCT/EP2013/054276, filed Mar. 4, 2013, and International PCT Patent Application Serial No. PCT/EP2012/059207, filed May 16, 2012, the entire contents of each of which are incorporated herein by reference.

FIELD OF THE INVENTION

The present invention relates to the field of pre-operative planning of trans-catheter valve implantation.

BACKGROUND

The left ventricle of the heart pumps the blood to the aorta through the aortic valve. Aortic (valve) stenosis is a pathology occurring when the aortic valve does not open fully because the leaflets calcify, thicken and stiffen and, as a result, the blood flow going from the heart to the systemic circulation decreases. Aortic stenosis manifests itself in elderly people, with a prevalence going from 1.3% in over 65 and 4% in over 85 year old people. Currently it is the most common valvular heart disease in the Western world and its prevalence is increasing with the aging population.

The standard treatment for an aortic stenosis is the Surgical Aortic Valve Replacement (SAVR) aiming at reproducing the correct function of the native valve with an implanted valve. This invasive procedure requires total anesthesia, sternotomy (open-heart surgery) and cardiopulmonary bypass (the blood is pumped and oxygenated using an external machine), and is associated with about 6% in-hospital mortality for over 65 year old patients. Moreover, at least one-third of the patients with severe aortic stenosis are denied valve surgery as the risks associated with surgery are too high.

Trans-catheter aortic valve implantation (TAVI) or trans-catheter aortic valve repair (TAVR) is a minimally-invasive procedure for treating aortic stenosis: (1) the valve (e.g. a bioprosthetic valve made of porcine pericardium sutured on a metal stent) is crimped inside a catheter, (2) the catheter is inserted, for example, in the femoral artery, (3) pushed upstream along the aorta up to the aortic annulus and (4) the new valve is deployed within the diseased native valve. TAVI has the potential of treating high-risk patients and replacing the SAVR with a minimally-invasive intervention (no need for open-heart surgery or cardiopulmonary bypass) which can be performed in e.g. about 80 minutes.

Main TAVI complications are vascular injury, stroke, cardiac injury (heart block, coronary obstruction, cardiac perforation), aortic regurgitation, cardiac conduction abnormalities and valve misplacement. Accurate pre operative planning is crucial to select the optimal device size and to anticipate potential difficulties.

Undersizing of a valve implant may lead to paravalvular aortic regurgitation, while oversizing may result in a rupture of the aortic annulus or in a suboptimal functional behavior of the implant. Currently available planning tools (Philips, Siemens, Pie Medical, Paeion) provide insights into the patient anatomy and can, for example, be used to determine the size of the aortic annulus, or to measure the distance between the valve plane and the coronary ostia. A problem with these tools is that they do not provide preoperative insights into the interaction between a certain implant device and the specific patient anatomy, and can thus not be used to predict complications such as regurgitation. Such insights are extremely valuable for interventional cardiologists.

Another problem is that is difficult to reconstruct native leaflets from e.g. CT images. In the currently deployed methods, an incomplete leaflet image is obtained, comprising gaps whereby the gaps represent a lack of data.

Document US 2011/0153286 A1 discloses a method and system for virtual percutaneous valve implantation. In one embodiment of the application a patient-specific anatomical model of a heart valve is estimated based on 3D cardiac medical image data. An implant model representing a valve implant is virtually deployed into the patient-specific anatomical model of the heart valve. A library of implant models, each modeling geometrical properties of a corresponding valve implant, can be maintained. The implant models maintained in the library can be virtually deployed into the patient specific anatomical model of the heart valve to select one of the implant models for use in a percutaneous valve implantation procedure.

US 2011/0153286 A1 does not provide a prediction of the mechanical behavior and interaction of the patient-specific aortic root, ascending aorta and aortic valve leaflets with the deployment of a valve implant. Said document also does not account for calcification of aortic valve leaflets. Neither does it provide a means to study the hemodynamic performance of an implant deployed in the aortic valve. Balloon-expandable devices whose deployment is based on permanent plastic deformations of the metal cannot be modeled.

There is a need for more precise valve sizing and positioning. Problem is that the aortic annulus is not circular, that the aortic annulus may deform and that calcium deposits may deform a valve frame.

Another problem is that the aortic root visualised with Computed Tomography (CT) imaging changes in shape and size after TAVI. Also the geometry of the stent frame of the TAV is affected by the stiffness of the aortic root, by the presence of stiff calcified regions and by the exact device position. Sub-optimal treatment planning can have two socio-economic effects.

At the one hand this gives higher costs for the health system. If the incorrect device/size of the TAV is chosen, the first TAVI procedure may fail and additional treatments, including a second TAVI procedure (valve-in-valve), SAVR, or rehospitalization may be necessary, with a considerable increase of the costs per patient. As a reference, one single TAVI procedure costs about 40 k Euro and the stented valve itself costs about 20 k Euro. At the other hand this leads to a lower prognosis. Sub-optimal treatment planning may result in peri-procedural complications, which affect both the life quality and the life expectancy of the patient. An oversized valve may rupture the annulus or dissect the aorta whereas an undersized valve may dislodge and migrate or can induce paravalvular regurgitation.

The aim of the present invention is to provide a solution to overcome at least part of the above mentioned disadvantages. The invention thereto aims to provide an improved method for preoperative insights into the interaction of an implant device and specific patient anatomy, for better prediction of complications, such as regurgitation, for better prediction of the hemodynamic performance of an implant deployed in an aortic valve, and for better patient selection and stratification. Also the invention aims to provide a web-based pre-operative planning service for TAVI using computer simulations that predict stent frame deformation and incomplete frame apposition, allowing to assess the risk on regurgitation and other complications such as coronary obstruction and conduction abnormalities prior to the intervention. Also the invention aims to give valuable insights for optimal device position, size and type.

In a further aspect, the invention aims to provide an improved stent device obtained by said method and a system for the execution of said method.

SUMMARY

In a first aspect, the present invention aims to provide a method for patient-specific virtual percutaneous implantation according to claim 1. The method allows accurate prediction of an optimal size of the implant, specifically adapted to the anatomy of the patient. Furthermore, correct positioning of the implant or optimal implantation depth is predicted and calculated. The method according the current invention will hence minimize the risk of peri- and post-procedural complications. The method will also improve patient-specific selection of implants.

In a second aspect, the present invention provides a method according to claim 17. The method allows for incorporating the impact of surrounding tissue and structures of the aorta and therefore improving accuracy of functional behavior prediction.

In a third aspect, the present invention provides an implant for virtual percutaneous implantation according to claim 19.

In a fourth aspect, the present invention provides a system for virtual percutaneous implantation according to claim 20.

DESCRIPTION OF THE FIGURES

Further features, advantages and objects of the present invention will become apparent for the skilled person when reading the following detailed description of embodiments of the present invention, when taken in conjunction with the figures of the enclosed drawings.

FIG. 4 and FIG. 5 depict an example of a patient-based anatomical model in which a device model is deployed using a simulation technique called finite element analysis.

DETAILED DESCRIPTION OF THE INVENTION

Figure 1:
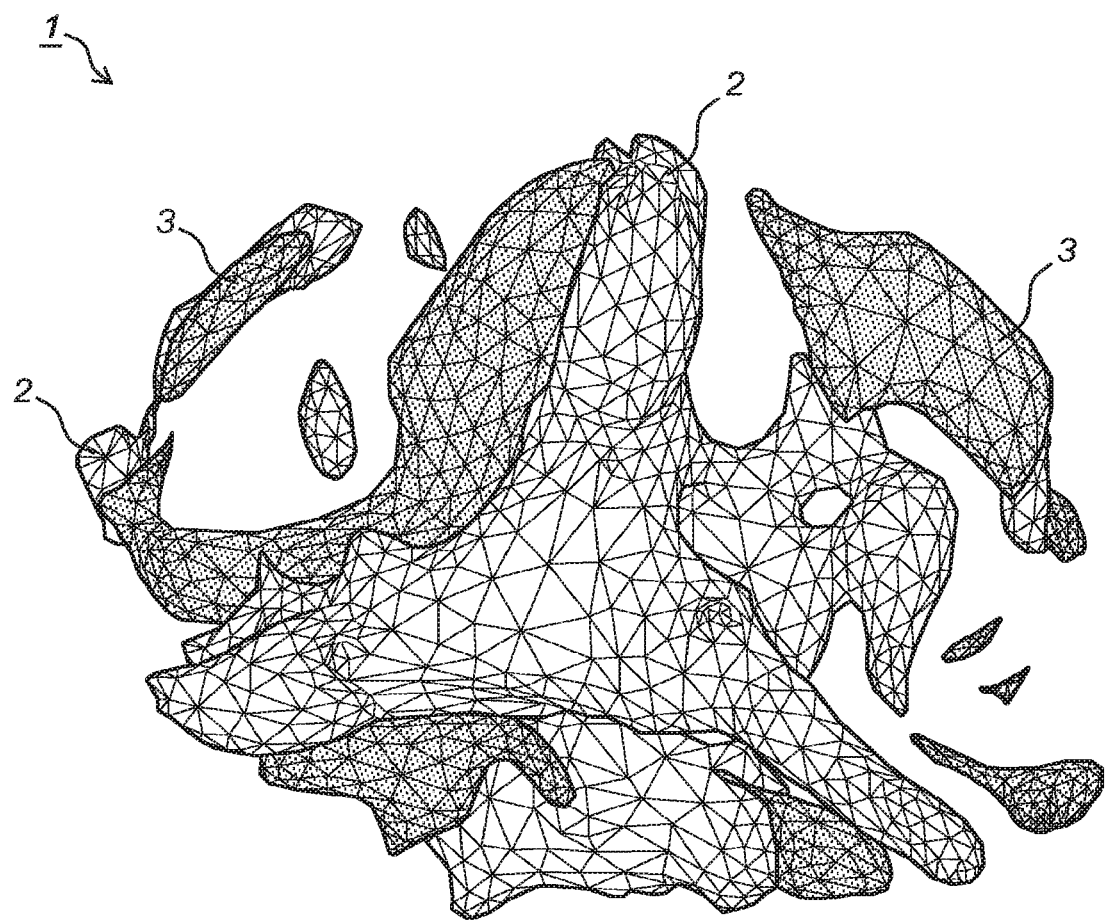
FIG. 1 describes a triangulated surface of the calcification in the leaflets and of the other leaflet tissue obtained using segmentation software. Automatic segmentation does not lead to a nice geometrical model of the three leaflets: parts are connected and gaps exist.

The present invention relates to a method for patient-specific virtual percutaneous implantation as well as to an implant obtained by the current method and a system employing the method of the current invention.

The present invention will be described on the basis of the figures and detailed description of the invention, which complete content is to be regarded as an integral part of the detailed description of the invention.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

"Point" and "node" as used herein are synonymous and are used interchangeable herein.

In a first aspect, the current invention comprises a method for patient-specific virtual percutaneous implantation, comprising:
  estimating a patient-specific anatomical model of a patient-specific aorta based on cardiovascular 2D or 3D medical image data comprising:
    a) using segmentation techniques to create a finite element aorta mesh based on 2D or 3D medical image data, said aorta mesh representing a patient-specific aorta, preferably comprising the aortic root and the ascending aorta;
    b) using segmentation techniques to create a finite element aortic valve mesh based on 2D or 3D medical image data, said aortic valve mesh representing a patient-specific aortic valve, comprising 2 or 3 valve leaflets;
    c) said patient-specific anatomical model comprising a patient-specific aorta model and a patient-specific aortic valve model;
    d) said patient-specific anatomical model comprises a finite element mesh wherein each element of said mesh is featured by a set of nodes wherein adjacent elements of said element comprise mutually shared nodes with said element, wherein said element is featured by tissue dependent parameters and wherein each element of said mesh can differ in tissue dependent parameters from an adjacent element of said element of said mesh;
  virtually deploying an implant model representing an implant into said patient-specific anatomical model, whereby e) for each of said valve leaflets, selecting a number of leaflet attachment points on said aorta mesh, f) for each of said valve leaflets, estimating a number of leaflet points;

g) for each of said valve leaflets providing a transformed leaflet mesh, wherein the elements of said transformed leaflet mesh are featured by normal or aberrant tissue parameters;

h) and wherein said patient-specific anatomical model of a blood channel comprises said transformed leaflet meshes.

Preferably, said transformed leaflet mesh is defined by said leaflet points and said leaflet nodes.

In a further aspect, the current invention comprises a method for patient-specific virtual percutaneous implantation, comprising:

estimating a patient-specific anatomical model of a patient-specific aorta based on cardiovascular 2D or 3D medical image data comprising:

a) using segmentation techniques to create a finite element aorta mesh based on 2D or 3D medical image data, said aorta mesh representing a patient-specific aorta, preferably comprising the aortic root and the ascending aorta;

b) using segmentation techniques to create a finite element aortic valve mesh based on 2D or 3D medical image data, said aortic valve mesh representing a patient-specific aortic valve, comprising 2 or 3 valve leaflets;

c) said patient-specific anatomical model comprising a patient-specific aorta model and a patient-specific aortic valve model;

d) said patient-specific anatomical model comprises a finite element mesh wherein each element of said mesh is featured by a set of nodes wherein adjacent elements of said element comprise mutually shared nodes with said element, wherein said element is featured by tissue dependent parameters and wherein each element of said mesh can differ in tissue dependent parameters from an adjacent element of said element of said mesh;

virtually deploying an implant model representing an implant into said patient-specific anatomical model, whereby e) for each of said valve leaflets, selecting a number of leaflet attachment points on said aorta mesh, f) for each of said valve leaflets, estimating a number of leaflet points;

g) for each of said valve leaflets, mapping said leaflet points and said leaflet nodes to a transformed leaflet mesh, wherein the elements of said transformed leaflet mesh are featured by normal or aberrant tissue parameters;

h) and wherein said patient-specific anatomical model of a blood channel comprises said transformed leaflet meshes.

The term 'cardiovascular 2D or 3D medical image data' as used herein is to be understood as all data related to an object to be analysed, said data is obtained by 2D or 3D imaging means. 2D or 3D imaging means may comprise, but are not limited to Nuclear Magnetic Resonance (NMR) imaging, Computed Tomography (CT) imaging, Positron Emission Tomography (PET), Single-photon emission computed tomography (SPECT) and echographic imaging. Preferably, said cardiovascular 2D or 3D medical image data is obtained through computed tomography.

The phrase "selecting a number of leaflet attachment points" as used herein is to be understood as a number of leaflet attachment points is chosen, selected and/or positioned on said aorta mesh.

The phrase "estimating a number of leaflet points" as used herein is to be understood as a number and/or the position of said leaflet points is estimated.

The term "mapping to" in the current invention is to be understood as assigning properties of said leaflet attachment points and said leaflet nodes to said transformed leaflet mesh. Preferably said properties comprise a 3-dimensional location. As such said transformed leaflet mesh is overlayed with said leaflet attachment points and said leaflet nodes.

The finite element mesh is programmed to contain the material and structural properties which define how the structure will react to certain loading conditions. Nodes are assigned at a certain density throughout the material depending on the anticipated stress levels of a particular area. Regions which will receive large amounts of stress usually have a higher node density than those which experience little or no stress. Points of interest may consist of: fracture point of previously tested material, fillets, corners, complex detail, and high stress areas.

A mesh transformation technique is used to create a grid or mesh of constant or variable thickness based on anatomical data of non-calcified leaflets, but calcifications may lead to higher local thicknesses. Preferably, said transformed leaflet mesh is an isoparametric leaflet mesh.

The method of the present invention is advantageous as it improves the accuracy of the medical intervention, clinical outcomes and reduces the associated risks. The method provides a better medical prediction of the functional behavior of the implant procedure. It allows to better understand the performance of an implant device or how to efficiently deploy an implant device into a patient. Also the method allows for an applicability of parameters sufficiently accurate for a broad population together with an acceptable calculation time. Testing new implant devices in realistic anatomies can be performed early in the development cycle to better understand the performance of a new device.

Preferably, said patient-specific model and implant model is a 3-dimensional finite element model.

It is also aim of the invention to provide pre-operative insights for different types of procedures (transcatheter aortic valve implantation, transcatheter mitral valve repair, endovascular aneurysm repair, left atrial appendage closure devices, etc.). The patient-specific model will then of course be based on a different part of the cardiovascular system, and the output will also be different.

Preferably, an alternative for said patient-specific aorta comprises a patient-specific blood vessel and said blood vessel comprises a valve.

The invention can also be applied for other heart valves, so not only the aortic valves. Therefore, the term "aorta" in underlying invention could also be interpreted as another patient-specific blood vessel e.g. the left atrium and/or ventricle, wherein "aortic valve" could be interpreted as the mitral valve and wherein corresponding patient-specific models are incorporated in the invention. Other valves such as the pulmonary valve in the pulmonary artery should be incorporated in the invention as well.

More preferably, said blood vessel comprises a patient-specific left atrium and/or ventricle, and said valve comprises a mitral valve.

More preferably, said blood vessel comprises a patient-specific right atrium and/or ventricle, and said valve comprises a tricuspid valve.

Preferably, stiffness elements are provided to a plurality of nodes of said aorta mesh, wherein a stiffness element induces a reacting force on the corresponding node of said aorta mesh, wherein said force is dependent on the displacement of said node or on the distance between said node and a fixed position equal or very close to the initial position of said node.

The deformation of the aorta and the annulus is affected by the surrounding tissue and structures. The mechanical impact of these tissues is important for a correct prediction of the stent structure obtained from simulated TAVI. The surrounding tissue could theoretically be included in the model by also segmenting based on the medical images. The making of such a model with all the surrounding tissues would be very time consuming, and simulation time would increase significantly. This method is advantageous as the virtual percutaneous implantation takes the impact of surrounding tissue and structures of the aorta into account, such as the stiffness or resistance. So if e.g. the aorta deforms, these stiffness elements (said displacements) will induce reacting forces which will work against this distortion. This way a better accuracy of simulation and therefore functional behavior prediction is achieved along with an acceptable calculation or simulation time.

More preferably, said reacting force depends on said displacements via a linear relationship. One can determine a spring constant k determining said linearity. A linear equation could therefore be Freact=k x, with Freact the reacting force and x said displacement. The spring constant k represents the stiffness or resistance of the surrounding tissue and structures of the aorta.

In another more preferred embodiment of the current invention, said reacting force depends on said displacement via a non-linear relationship.

More preferably, between different zones of said aorta mesh different stiffnesses or dependencies are assigned. Said different zones can have different material or tissue dependent properties.

Preferably, said steps a) and b) of the method according to the current invention further comprise:
  manually adjusting said leaflet attachment points and/or manually adjusting said leaflet points.

Preferably, an alternative for said patient-specific anatomical model comprises a patient-based anatomical model wherein said steps a, b and c are replaceable by:
  creating a finite element aorta mesh based on 2D or 3D medical image data, said aorta mesh representing a patient-based aorta, preferably comprising the aortic root and the ascending aorta;
  creating a finite element aortic valve mesh based on 2D or 3D medical image data, said aortic valve mesh representing a patient-based aortic valve, comprising 2 or 3 valve leaflets;
  said patient-based anatomical model comprising a patient-based aorta model and a patient-based aortic valve model (43).

The term 'patient-based model' as used herein is to be understood as a generic and/or parametric adaptable model. Based on measurement(s) and/or 2D or 3D medical images of a patient, certain parameters will be determined for the patient-based model.

It is advantageous as a patient-based anatomical model can also give insights into pre-operative planning of transcatheter valve implantation, without the need of segmentation techniques.

Preferably, the method according to the current invention further comprises:
  overlaying said transformed leaflet meshes with said aortic valve mesh;
  creating an aberrant leaflet mesh, comprising elements wherein said elements overlap with said aortic valve mesh and wherein said elements do not overlap with said transformed leaflet meshes and wherein said elements are featured by aberrant tissue parameters; wherein said patient-specific anatomical model of a blood channel comprises said transformed leaflet meshes and said aberrant leaflet mesh.

It is advantageous as the method also accounts for aberrant tissue such as e.g. calcifications for patients with aortic stenosis. This leads to a more accurate patient-specific model, which will give rise to better functional behavior prediction and clinical outcomes and again reduces the associated risks.

In a preferred embodiment, said implant model will comprise a skirt and leaflet elements.

In a more preferred embodiment, said implant model will comprise a stent, to be implanted in a passage or conduit of the body of the patient. In the current invention, said passage or conduit is preferably a vessel, such as an aorta.

More preferably, said implant model comprises a finite element mesh wherein each element of said mesh is featured by a set of nodes wherein adjacent elements of said element comprise mutually shared nodes with said element, wherein said element is featured by material dependent parameters and wherein each element of said mesh can differ in material dependent parameters from an adjacent element of said element of said mesh.

It is advantageous to take into account different material parameters in order to provide even more accurate results in functional behavior prediction.

In a further preferred embodiment of the current invention, the method step of virtually deploying an implant model representing an implant into the patient-specific anatomical model comprises a three-dimensional finite element analysis. The finite element method (FEM) (its practical application often known as finite element analysis (FEA)) is a solution technique based on subdividing the volume into a large number of small elements of simple shape, the behavior of which can be described in function of a small number of variables at a limited number of points (nodes) of the element. For steady state problems this reduces the partial differential equations to a large set of algebraic equations which can be easily solved. Time dependent problems will result in a set of ordinary different equations in time which can numerically be integrated using standard techniques, like finite difference methods.

Each FEA program may come with an element library, or one is constructed over time. Some sample elements are rod elements, beam elements, plate/shell/composite elements, shear panel, solid elements, spring elements, mass elements, rigid elements or viscous damping elements.

Preferably, said tissue dependent parameter and/or a material dependent parameter is chosen from the following group of parameters: Poisson's ratio, Young's modulus, density, shear modulus, yield stress, ultimate stress, elastoplastic parameter, energy density function, material damage parameter, superelastic material parameter, shape-memory material parameter, isotropic material parameter and anisotropic material parameter.

It is aim of the invention to provide patient-specific models sufficiently accurate by taking into account mechanical material properties of e.g. different layers, areas of layers, etc., together with a sufficiently fast calculating time.

The method of the current invention comprises furthermore preferably a step whereby a blood mesh is created, comprising a finite volume mesh, wherein the blood mesh describes the volume within said patient-specific anatomical model exclusive said deployed implant model; and whereby the blood flow is calculated for said blood mesh using computational fluid dynamics analysis.

The finite volume method is a method for representing and evaluating partial differential equations in the form of algebraic equations [LeVeque, 2002; Toro, 1999]. Similar to the finite difference method or finite element method, values are calculated at discrete places on a meshed geometry. "Finite volume" refers to the small volume surrounding each node point on a mesh. In the finite volume method, volume integrals in a partial differential equation that contain a divergence term are converted to surface integrals, using the divergence theorem. These terms are then evaluated as fluxes at the surfaces of each finite volume. Because the flux entering a given volume is identical to that leaving the adjacent volume, these methods are conservative. Another advantage of the finite volume method is that it is easily formulated to allow for unstructured meshes. The method is used in many computational fluid dynamics packages. For more info on the finite volume method, we refer integrally to Eymard et al., Handbook of Numeral Analysis (2000).

In a further preferred step, the amount of paravalvular regurgitation is predicted based on a geometrical analysis of said blood mesh. Hemodynamic performance of the implant can be predicted by quantifying paravalvular leakages, valve insufficiency, and effective orifice and systolic gradients across the aortic prosthesis.

It is advantageous to predict paravalvular regurgitation as it has been associated with increased mortality. This regurgitation is the result of several factors related to the aortic root anatomy and its relation to the implanted prosthesis including the shape and size of the aortic annulus, degree of annular and leaflet calcifications, left-ventricular outflow tract (LVOT) anatomy, and the prosthesis/annulus discongruence.

More preferably, the position and the orientation for implanting the implant is determined based on the complications predicted by said virtually deployed implant model. Even more preferably, said complications comprise the amount of paravalvular regurgitation, obstruction of coronary artery and/or electrical conductivity problems (e.g. related to an implementation of a pacemaker). Most preferably, the position and the orientation for implanting the implant is determined based on the amount of paravalvular regurgitation predicted by said virtually deployed implant model.

This will improve the accuracy of the medical deploying intervention, clinical outcomes and reduce associated risks.

In a further preferred step, the risk of coronary obstruction, annular rupture and conduction abnormalities is predicted by virtually deploying an implant model representing an implant into the patient-specific anatomical model.

The model parameters of the implant model and the patient-specific anatomical model are calibrated by comparing said calculations with postoperative medical image data.

It is advantageous to determine or calibrate model parameters and specifications in order to provide improving and/or optimal results for a broad population of patients or a number of subpopulations of patients. These parameters can be material dependent parameters, tissue dependent parameters, layer thicknesses, etc.

Preferably, said virtually deploying of an implant model representing an implant into said patient-specific anatomical model comprises:
  maintaining a library of implant models, each modeling geometrical and/or material properties of a corresponding implant; and
  virtually deploying each of a plurality of the implant models maintained in the library into the patient specific anatomical model to select one of the plurality of the implant models maintained in the library for a percutaneous implantation procedure.

By providing a database of device models representing the actual device geometry and having similar mechanical behavior, interventional cardiologists or hospitals can select optimal device size and type for patients.

More preferably, this will equally comprise:
  maintaining a library of patient-specific anatomical models, each modeling geometrical and/or material properties of a corresponding patient-specific anatomical blood channel; and
  virtually deploying said implant model into each of a plurality of the patient specific anatomical models maintained in said library to evaluate said implant model for a percutaneous implantation procedure.

This method is advantageous for the development of implant models based on the functional behavior on a plurality of patient specific anatomical models. This leads to better, cheaper, more effective implants, an optimal understanding of an implant model and therefore less risk for patients.

Taking the expansion of an implant model into account will lead to a better understanding in functional behavior of the implant model.

In a second aspect, the current invention discloses an implant for virtual percutaneous implantation, obtained by the method as explained above.

Preferably, said implant for virtual percutaneous implantation is obtained by selecting an implant model based on the amount of paravalvular regurgitation predicted by said virtually deployed implant model.

In a preferred embodiment, the valve implant is balloon-expendable or self-expendable.

In a third aspect, the current invention discloses a method for patient-specific virtual percutaneous implantation, comprising:
  estimating a patient-specific anatomical model of a patient-specific aorta based on cardiovascular 2D or 3D medical image data comprising:
    a) using segmentation techniques to create a finite element aorta mesh based on 2D or 3D medical image data, said aorta mesh representing a patient-specific aorta, preferably comprising the aortic root and the ascending aorta;
    b) using segmentation techniques to create a finite element aortic valve mesh based on 2D or 3D medical image data, said aortic valve mesh representing a patient-specific aortic valve, comprising 2 or 3 valve leaflets;
    c) said patient-specific anatomical model comprising a patient-specific aorta model and a patient-specific aortic valve model;
    d) said patient-specific anatomical model comprises a finite element mesh wherein each element of said mesh is featured by a set of nodes wherein adjacent elements of said element comprise mutually shared nodes with said element, wherein said element is featured by tissue dependent parameters and wherein each element of said mesh can differ in tissue dependent parameters from an adjacent element of said element of said mesh;

virtually deploying an implant model representing an implant into said patient-specific anatomical model, whereby stiffness elements are provided to a plurality of nodes of said aorta mesh, wherein a stiffness element induces a reacting force on the corresponding node of said aorta mesh, wherein said force is dependent on the displacement of said node or on the distance between said node and a fixed position equal or very close to the initial position of said node.

The deformation of the aorta and the annulus is affected by the surrounding tissue and structures. The mechanical impact of these tissues is important for a correct prediction of the stent structure obtained from simulated TAVI. The surrounding tissue could theoretically be included in the model by also segmenting based on the medical images. The making of such a model with all the surrounding tissues would be very time consuming, and simulation time would increase significantly. This method is advantageous as the virtual percutaneous implantation takes the impact of surrounding tissue and structures of the aorta into account, such as the stiffness or resistance. So if e.g. the aorta deforms, these stiffness elements (said displacements) will induce reacting forces which will work against this distortion. This way a better accuracy of simulation and therefore functional behavior prediction is achieved along with an acceptable calculation or simulation time.

Preferably, said reacting force depends on said displacements via a linear relationship. One can determine a spring constant k determining said linearity. A linear equation could therefore be Freact=k·x, with Freact the reacting force and x said displacement. The spring constant k represents the stiffness or resistance of the surrounding tissue and structures of the aorta.

In another preferred embodiment of the current invention, said reacting force depends on said displacement via a non-linear relationship.

Preferably, between different zones of said aorta mesh different stiffnesses or dependencies are assigned. Said different zones can have different material or tissue dependent properties.

Preferably, an alternative for said patient-specific aorta comprises a patient-specific left atrium and left atrial appendage and wherein said steps b and c are replaceable by:
said patient-specific anatomical model comprising a patient-specific aorta model.

The left atrium comprises a muscular pouch called the "left atrial appendage". Some people can have blood clots formed in this appendix. To prevent these clots from going into the bloodstream, implant devices exist that can be inserted in this appendix in order to blocking clots. This procedure is called "left atrial appendage closure (LAAC)". The invention therefore likewise can improve this LAAC intervention and procedure.

Preferably, an alternative for said patient-specific aorta comprises a patient-specific blood vessel and said blood vessel comprises a valve.

The invention can also be applied for other heart valves, so not only the aortic valves. Therefore, the term "aorta" in underlying invention could also be interpreted as another patient-specific blood vessel e.g. the left atrium and/or ventricle, wherein "aortic valve" could be interpreted as the mitral valve and wherein corresponding patient-specific models are incorporated in the invention. Other valves such as the pulmonary valve in the pulmonary artery should be incorporated in the invention as well.

More preferably, said blood vessel comprises a patient-specific left atrium and/or ventricle, and said valve comprises a mitral valve.

More preferably, said blood vessel comprises a patient-specific right atrium and/or ventricle, and said valve comprises a tricuspid valve.

In a final aspect, the current invention discloses a system for virtual percutaneous implantation, comprising:
a storage medium comprising 2D or 3D medical image data;
a secured server;
a computing system implemented with a method for virtual percutaneous implantation according to the current invention.

Preferably, said storage medium, said secured server and said computing system are web-connected.

It is the aim of the current invention to provide a report to the medical doctor, comprising:
figures of the implanted device(s),
colour plots of the incomplete apposition of the device(s). These plots give insight into possible paravalvular leaks,
forces on the annulus f aortic root and stresses in the annulus/aortic root,
a quantitative value derived from the computational fluid dynamics analysis the geometrical analysis of the blood mesh) reflecting the amount of regurgitation.

It is also the aim of the current invention to provide 3D models showing the interaction between one or more implant models representing implants and a patient-specific anatomical model.

The values currently used in clinical practice describe the amount of regurgitation (grade 0, 1, 2, 3 or 4; grade 0 corresponds with no or minimal regurgitation, grade 1 is mild regurgitation, grade 2 is moderate regurgitation, grade 3 is moderately severe regurgitation, grade 4 is severe regurgitation). In clinical practice, aortic regurgitation after TAVI can be observed using medical imaging (angiogram, echo). The physicians then assign a grade to the amount of regurgitation that they observe. In the current invention, a quantitative value based on, for example, the volume of backflow (regurgitation) during diastole (when the valve is closed) will be derived from the computational fluid dynamics analyses

EXAMPLES

Example 1

In a preferred embodiment of the invention an anatomical model of the aortic root and of the ascending aorta is generated from CT images using traditional image segmentation methods or software. The resulting 3D anatomical model is a triangulated surface mesh.

FIG. 1 describes a triangulated surface of the calcification in the leaflets and of the other leaflet tissue obtained using segmentation methods. As mentioned, automatic segmentation does not lead to a nice geometrical model of the three leaflets: parts are connected and gaps exist. FIG. 1 shows an aortic valve mesh 1, a triangulated finite element mesh of normal leaflet tissue 2 and a triangulated finite element mesh of calcificied leaflet tissue 3. Parts of the native leaflets are visible on CT images but gaps exist. It is therefore difficult to reconstruct these regions using segmentation methods. In contrast to known methods, valves according to the present invention are not based on 4 estimated landmarks, and do not use a hyperbolic paraboloid. In the method according to the current invention, each valve is defined by, for example, 25 points in order to accurately model the real valve geometry:

For example, 13 points, lying on the attachment edge, are manually picked on the previously generated aorta model, the other 12 points are then initially estimated based on the 13 picked points, all points are then manually adjusted in order to match the shape of the valve model with the geometrical valve information obtained by segmentation (see FIG. 1).

Figure 2:
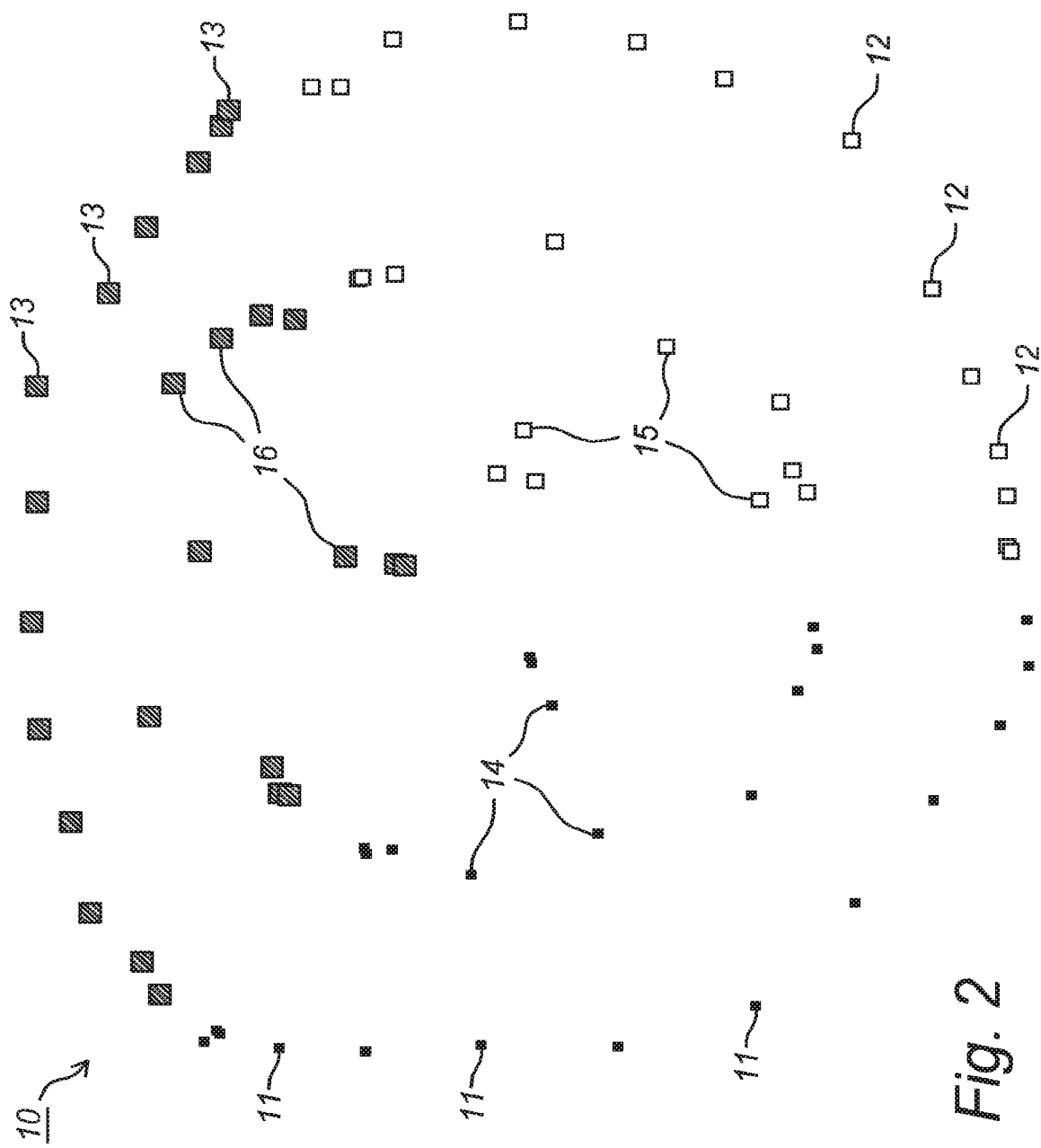
FIG. 2 describes points that define the leaflet geometry. Each leaflet is defined by, for example, 25 points. A subset, for example 13, of these points lies on the attachment edge that connects the valve with the aortic root.

FIG. 2 describes points that define the leaflet geometry. Each leaflet is defined by, for example, 25 points. For example, 13 of these points lie on the attachment edge that connects the valve with the aortic root. FIG. 2 shows a 3-leaflet valve node geometry 10, a first leaflet node on attachment edge 11, an estimated leaflet 1 node 14, a leaflet 2 node on attachment edge 12, a second estimated leaflet node 15, a leaflet 3 node on attachment edge 13 and a third estimated leaflet 3 node 16.

Figure 3:
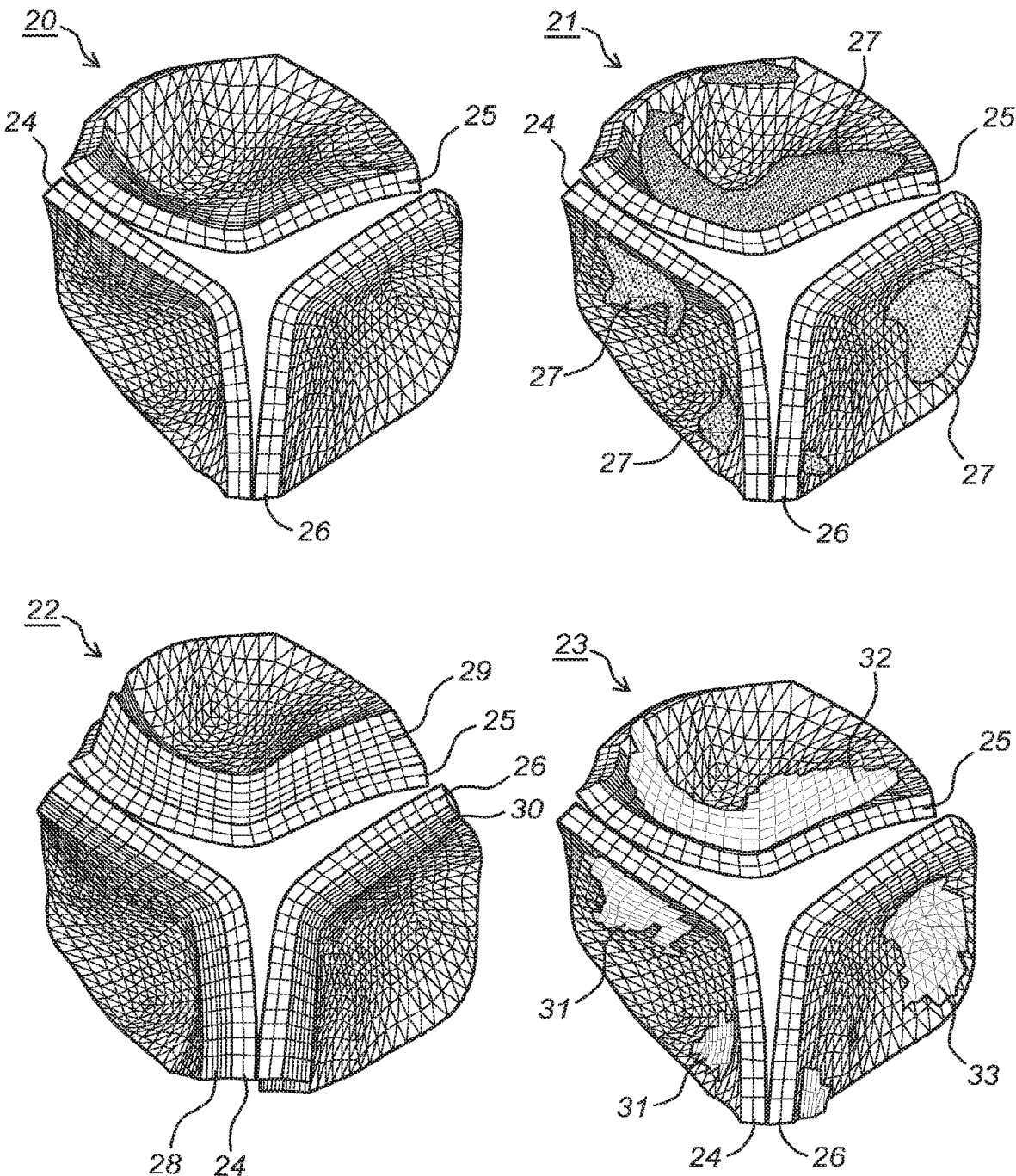
FIG. 3 shows an illustration of the different steps of the method of the current invention to generate a computational mesh or grid of the calcified leaflets.

FIG. 3 shows an illustration of the different steps in the proposed method to generate a computational mesh or grid of the calcified leaflets. A generic leaflet mesh is transformed using an isoparametric transformation to create a grid or mesh of constant or variable thickness. The thickness is based on anatomical data of non calcified leaflets, but calcifications may lead to higher local thicknesses. In the top right panel of FIG. 3, the calcification obtained through image segmentation is overlayed with the leaflet mesh. In order to incorporate the calcification in the computational mesh or grid, additional layers of elements are added. From these additional layers of elements, only the elements within the calcified regions are kept in the final model.

Element 20 depicts the transformed finite elements 24 of leaflet 1, the transformed finite elements 25 of leaflet 2 and the transformed finite elements 26 of leaflet 3. Element 21 comprises overlayed calcified region elements 27. Element 22 comprises an additional layer finite elements 28 of leaflet 1, an additional layer finite elements 29 of leaflet 2 and an additional layer finite elements 30 of leaflet 3. Element 23 comprises calcified elements 31 of leaflet 1, calcified elements 32 of leaflet 2 and calcified elements 33 of leaflet 3.

FIG. 4 describes examples of a patient-based anatomical model in which a device model is deployed using a simulation technique called finite element analysis.

Example 70 comprises a native ascending aorta model 40, a native aortic root model 41, a native left ventricle 42, a native aortic leaflet model 43, a native aortic valve annulus 44 and a native left coronary artery 45. Example 71 comprises a predilated balloon 46. Example 72 comprises an implant model 47.

Figure 5:
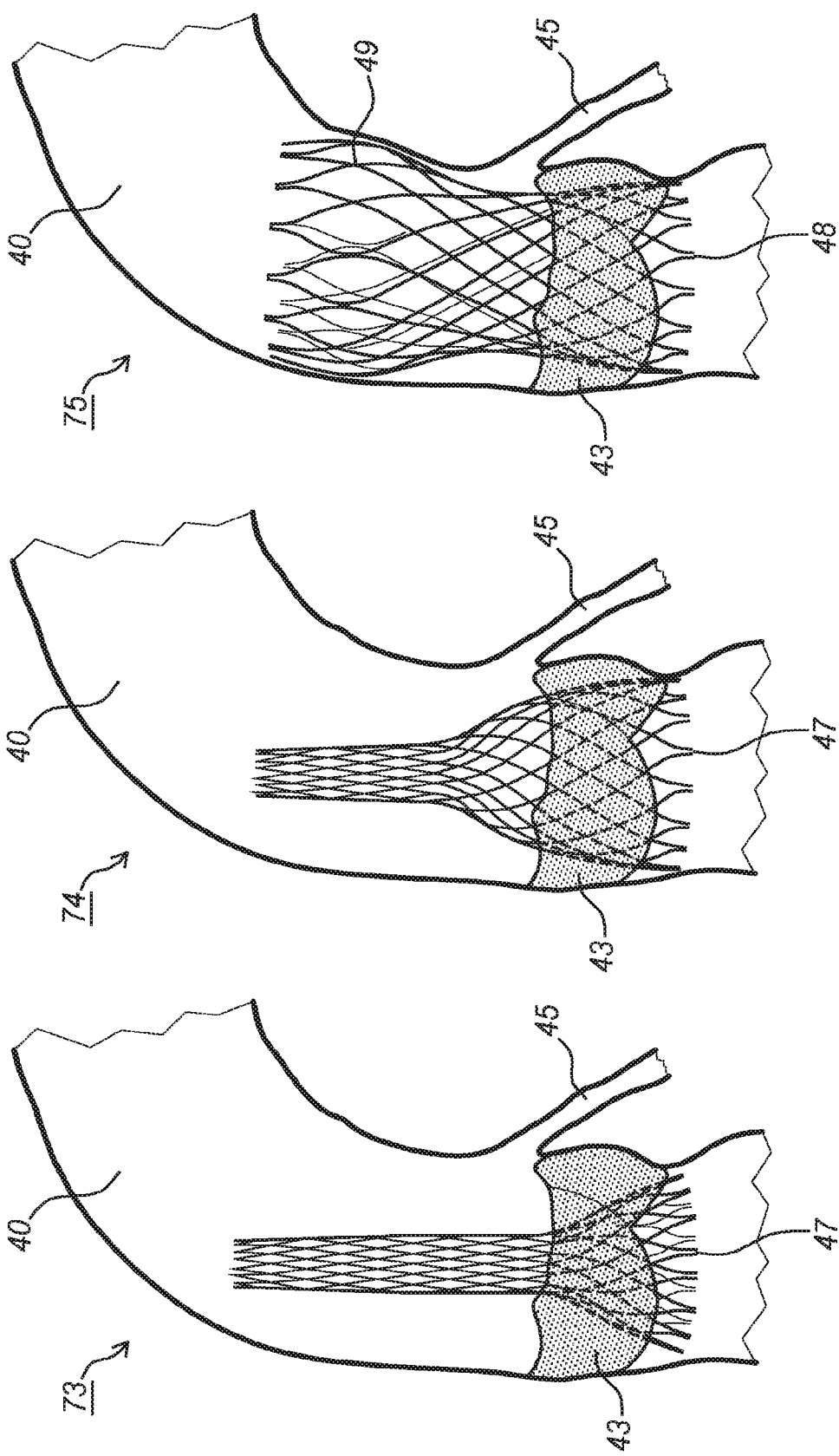

An example of a simulated deployment of a self-expandable CoreValve (Medtronic) transcatheter aortic valve is shown in FIGS. 4 and 5. A predilatation of the calcified valve can be included in the simulation process as depicted in FIG. 4 (valvuloplasty). This leads to a weakening of the calcifications and is often performed in clinical practice. Similarly, a postdilatation of the stent frame, sometimes performed to improve the expansion of the implanted device, can be included in the simulation process (not shown). FIG. 4 shows an example of a patient-based anatomical model in which a predilatation is performed using a simulation technique called finite element analysis and a device model is positioned.

FIG. 5 shows an example of a patient based anatomical model in which a device model is deployed using a simulation technique called finite element analysis. The interaction with the surrounding anatomical structures (e.g. heart muscle) is taken into account in the model by adding springs on the aortic surface. The spring stiffness can be controlled and can have different values in different regions (e.g. higher stiffness near the aortic annulus). Other important parameters in the model are the material behaviour of the different components (leaflets, calcifications on the leaflets, aortic tissue) and the thickness of the aortic wall. In our model, different wall behaviour and thickness can be assigned to different regions of the aorta. Example 73 and example 74 comprise an implant model 47. Example 75 comprises a deployed implant model 48 and a device frame model 49.

Figure 6:
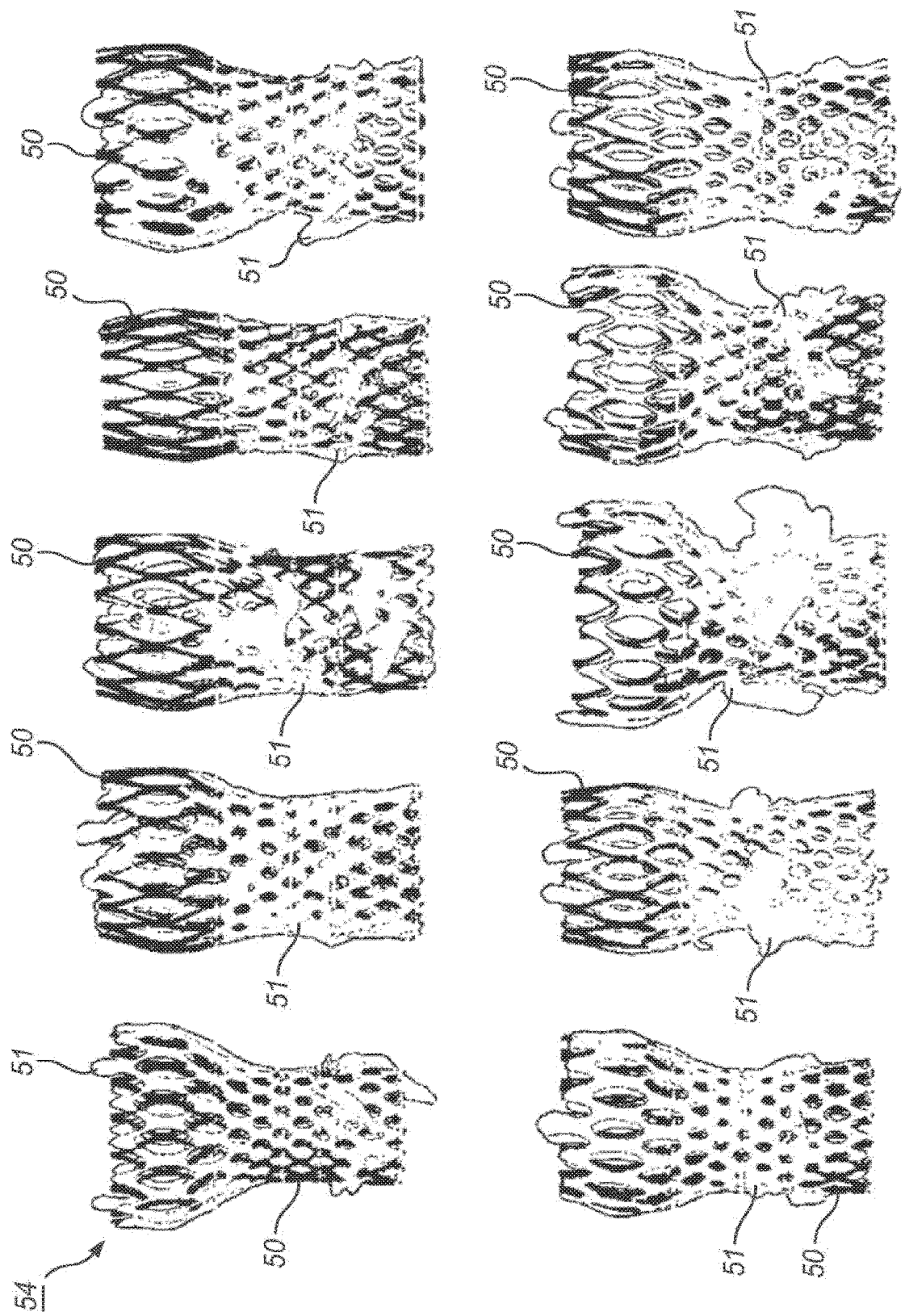
FIG. 6 depicts an overview of 10 deformed CoreValve (Medtronic) stent frames.

FIG. 6 describes an overview of the 10 deformed CoreValve stent frames. FIG. 6 shows a predicted stent frame 50, a 3D reconstruction of stent frame based on post-operative CT data 51 and 10 deformed CoreValve stent frames 54. The model parameters have been calibrated by using pre- and post-operative CT data of minimum 10 patients that underwent TAVI. A patient-specific model has been created for all these patients and the same TAVI procedure was performed using finite element computer simulations as it was done in the hospital (same balloon for pre-dilatation and postdilatation, same size of the CoreValve device, same device position, etc.). Further calibration will be done by adding more patients to the database. The model parameters were adjusted until a good correlation was obtained between the deformed stent frame as predicted by the simulations and the geometry of the stent frame as observed from the post-operative image data (see FIGS. 5 and 6).

Figure 7:
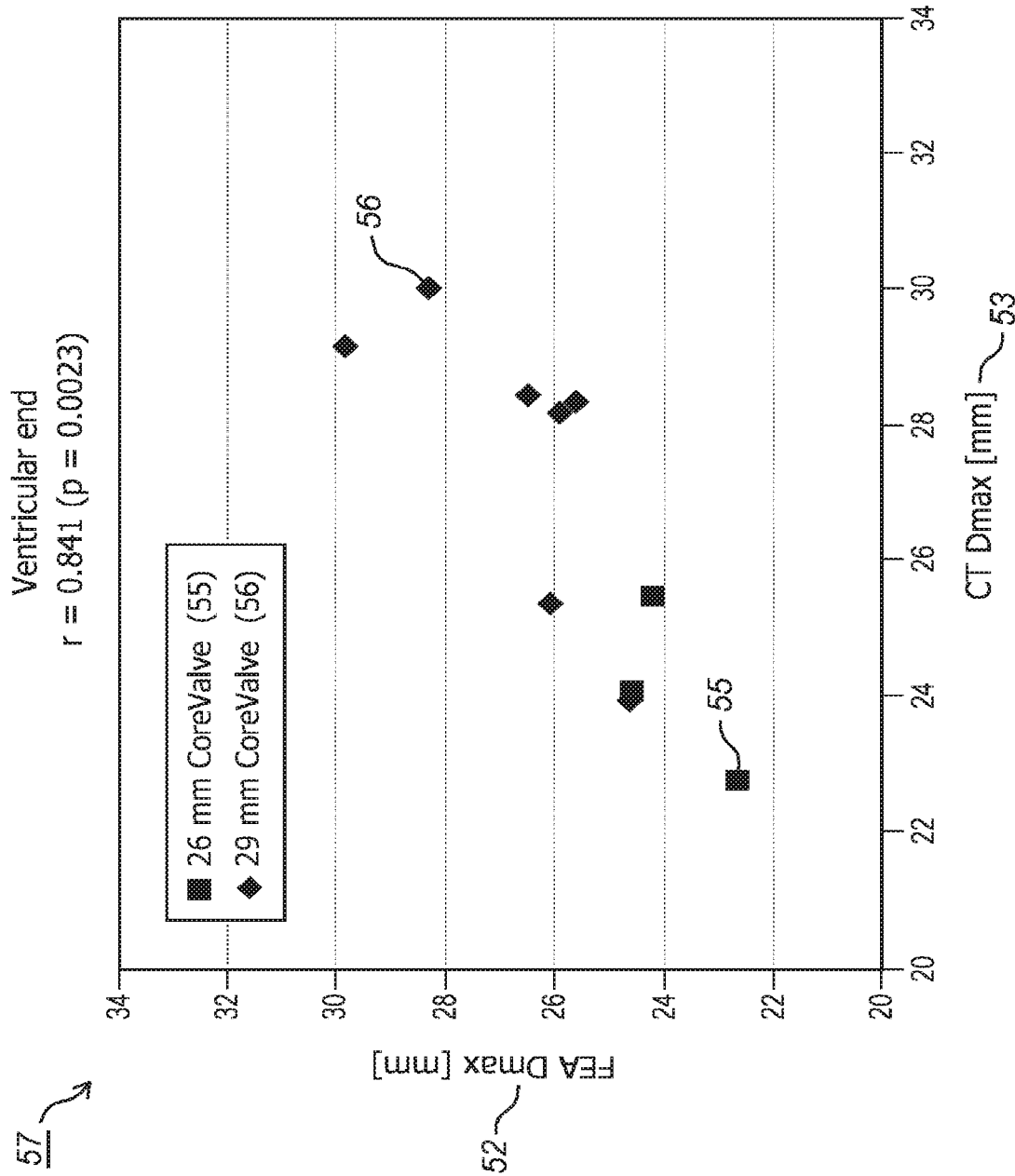
FIG. 7 depicts a correlation between the maximal diameter (Dmax) of the stent frame measured at the ventricular end. The Dmax measured on the post-operative CT data is plotted on the X-axis, while the Dmax predicted by the finite element analyses (FEA) is given on the Y-axis.

FIG. 7 describes the correlation between the maximal diameter (Dmax) of an elliptic cross section of the stent frame measured at the ventricular end. The Dmax measured on the post-operative CT data (Dmax, CT 53) is plotted on the X-axis, while the Dmax predicted by the finite element analyses (Dmax, predicted (FEA) 52) is given on the Y-axis. 57: CoreValve. 26 mm stent 55 and CoreValve. 29 mm stent 56.

Figure 8:
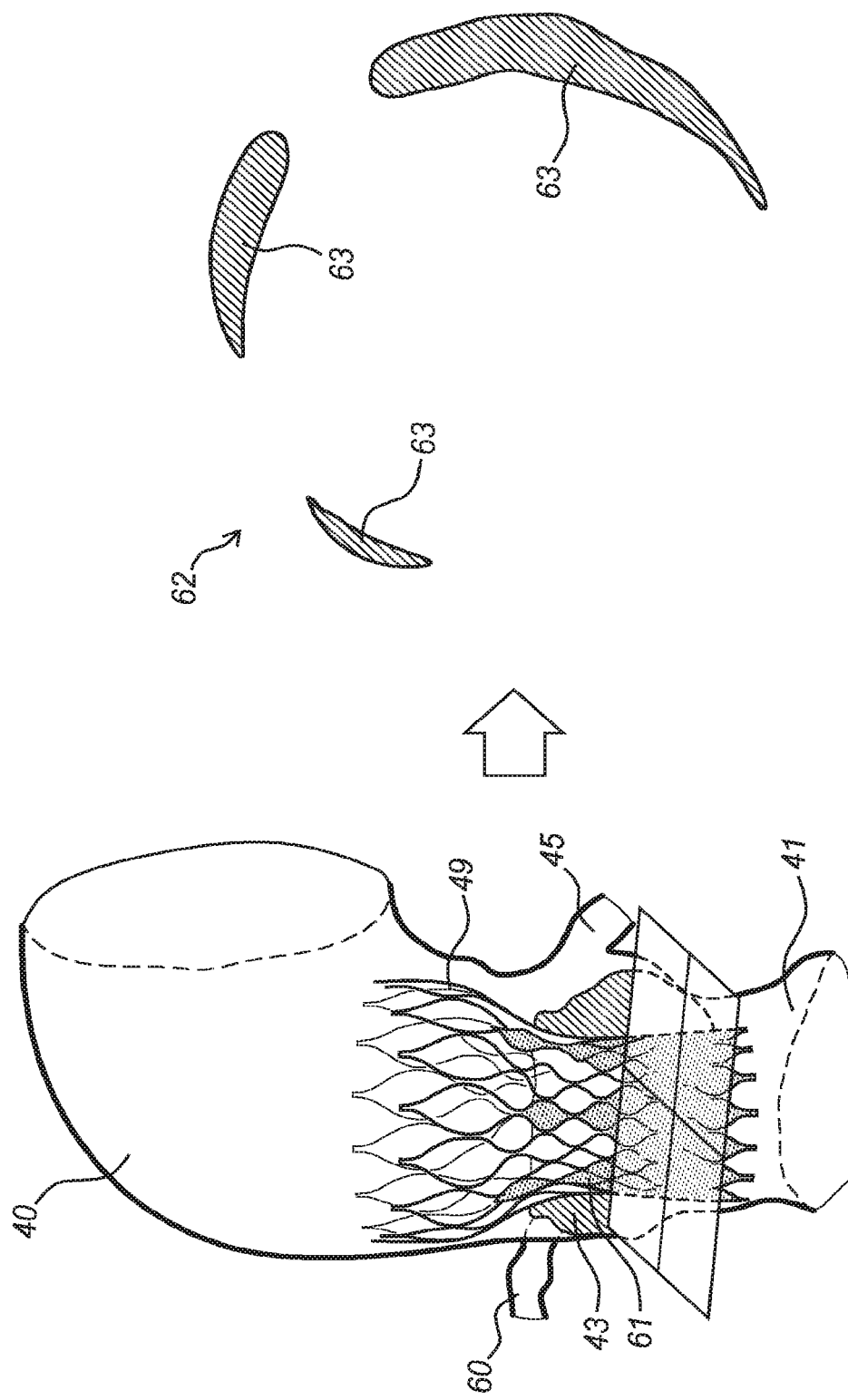
FIG. 8 depicts the deformed structures from the finite element analysis (left panel). The flow during diastole can then be modeled using computational fluid dynamics to assess the amount of regurgitation. The right panel shows the flow in the plane indicated in the left panel.

FIG. 8 depicts the deformed structures from the finite element analysis (left panel). The flow during diastole can then be modeled using computational fluid dynamics to assess the amount of regurgitation. The right panel shows the flow in the plane indicated in the left panel.

In FIG. 8 following elements are shown: a native ascending aorta model 40, a native aortic root model 41, a native left ventricle 42, a native aortic leaflet model 43, a native left coronary artery 45, a right coronary artery 60, an implant device leaflet 61, a device frame model 49, a computational grid of the fluid domain 62 with a computed flow during diastole 63.

Based on the deformed structures (stent, aorta, native leaflets, etc.) obtained from the finite element simulation, a computational grid of the fluid domain is created. The generation of such a grid or mesh is complex but required to model the backflow or regurgitation using computational fluid dynamics. The following method has been developed to create this computational mesh: —a regular grid of small cubes or hexahedral elements is created within the bounding box of the patient-based model—the cubes within the fluid domain are automatically detected. Other approaches are also possible.

Although the present invention has been described with reference to preferred embodiments thereof, many modifications and alternations may be made by a person having

The invention claimed is:

1. A computer-implemented method for evaluating the placement of a prosthetic device in a patient's body, comprising:
   obtaining a plurality of digital images of a patient's cardiac anatomy;
   obtaining a digital model of a prosthetic cardiac device;
   generating, from the plurality of digital images, a patient-specific digital depiction of the patient's cardiac anatomy including a cardiac anatomical structure in fluid communication with an adjacent anatomical structure, using a computer system;
   virtually placing the digital model of the prosthetic cardiac device within the cardiac anatomical structure of the patient-specific digital depiction;
   calculating, using the computer system, a measure of blood flow obstruction to the adjacent anatomical structure of the patient-specific digital depiction resulting from the placement of the digital model of the prosthetic cardiac device; and
   generating, using the computer system, information to indicate the measure of blood flow obstruction to the adjacent anatomical structure of the patient-specific digital depiction resulting from the placement of the digital model of the prosthetic cardiac device.

2. The method of claim 1, further comprising revising the placement of the digital model of the prosthetic cardiac device responsive to the measure of blood flow obstruction to the adjacent anatomical structure.

3. The method of claim 1, wherein for a given placement, calculating, using the computer system, the measure of blood flow obstruction to the adjacent anatomical structure comprises:
   determining a cross-sectional area of the adjacent anatomical structure of the patient-specific digital depiction after placement of the digital model of the prosthetic cardiac device; and
   calculating, using the computer system, the measure of blood flow obstruction based on the determined cross-sectional area.

4. The method of claim 1, wherein virtually placing of the digital model of the prosthetic cardiac device within the cardiac anatomical structure of the patient-specific digital depiction further comprises selecting a digital model of a preferred prosthetic cardiac device from amongst a plurality of digital models; and
   wherein calculating, using the computer system, the measure of blood flow obstruction to the adjacent anatomical structure comprises, calculating, using the computer system, for the digital model of the preferred prosthetic cardiac device, the measure of blood flow obstruction to the adjacent anatomical structure.

5. The method of claim 1, wherein the cardiac anatomical structure of the patient-specific digital depiction is an aortic root of the patient, the adjacent anatomical structure includes a coronary artery ostium, and calculating, using the computer system, the measure of blood flow obstruction to the adjacent anatomical structure resulting from the placement of the digital model of the prosthetic cardiac device comprises calculating, using the computer system, the measure of obstruction of the blood flow to the coronary artery ostium based on placement of the digital model of the prosthetic cardiac device within the aortic root.

6. The method of claim 1, wherein the cardiac anatomical structure of the patient-specific digital depiction is a valve annulus of the patient, the adjacent anatomical structure includes a left ventricular outflow tract, and calculating, using the computer system, the measure of blood flow obstruction to the adjacent anatomical structure resulting from the placement of the digital model of the prosthetic cardiac device comprises calculating, using the computer system, the measure of blood flow obstruction through the left ventricular outflow tract based on placement of the digital model of the prosthetic cardiac device within the valve annulus.

7. The method of claim 1 further comprising, following virtually placing the digital model of the prosthetic cardiac device within the cardiac anatomical structure of the patient-specific digital depiction:
   generating a revised patient-specific digital depiction based on computation of a deformation of the cardiac anatomical structure caused by the placement of the digital model of the prosthetic cardiac device, the revised patient-specific digital depiction including an impact of the deformation on the adjacent anatomical structure.

8. The method of claim 7, wherein the deformation of the cardiac anatomical structure is computed using finite element analysis.

9. The method of claim 1, wherein obtaining the plurality of digital images of the patient's cardiac anatomy comprises importing portions of CT-scans of the patient's cardiac anatomy.

10. The method of claim 9, wherein the cardiac anatomical structure comprises a human heart valve, and generating the patient-specific digital depiction of the cardiac anatomical structure further comprises generating a patient-specific digital depiction of a valve leaflet of the human heart valve using a plurality of leaflet attachment points.

11. A system for evaluating the placement of a prosthetic device in a patient's body, comprising:
    a processor; and
    a storage device having instructions stored therein, wherein the processor is configured to access the storage device and execute the instructions stored therein, wherein the instructions are configured to:
       accept a plurality of digital images of a patient's cardiac anatomy;
       retrieve from the storage device a digital model of a prosthetic cardiac device;
       generate from the plurality of digital images a patient-specific digital depiction of the patient's cardiac anatomy including a cardiac anatomical structure in fluid communication with an adjacent anatomical structure;
       for a virtual placement of the digital model of the prosthetic cardiac device within the cardiac anatomical structure of the patient-specific digital depiction, calculate a measure of blood flow obstruction to the adjacent anatomical structure of the patient-specific digital depiction resulting from the placement of the digital model of the prosthetic cardiac device; and
       generate information to indicate the measure of blood flow obstruction to the adjacent anatomical structure of the patient-specific digital depiction resulting from the placement of the digital model of the prosthetic cardiac device.

12. The system of claim 11, wherein the processor is further configured to revise the placement of the digital model of the prosthetic cardiac device responsive to the measure of blood flow obstruction to the adjacent anatomical structure.

13. The system of claim 11, wherein for a given placement, the processor is configured to calculate the measure of blood flow obstruction to the adjacent anatomical structure by:
  determining a cross-sectional area of the adjacent anatomical structure after placement of the digital model of the prosthetic cardiac device; and
  calculating the measure of blood flow obstruction based on the determined cross-sectional area.

14. The system of claim 11, wherein the processor is configured to:
  virtually place the digital model of the prosthetic cardiac device within the cardiac anatomical structure by selecting a digital model of a preferred prosthetic cardiac device from amongst a plurality of digital models; and
  calculate the measure of blood flow obstruction to the adjacent anatomical structure resulting from placement of the digital model of the preferred prosthetic cardiac device.

15. The system of claim 11, wherein the cardiac anatomical structure of the patient-specific digital depiction is an aortic root of the patient and the adjacent anatomical structure includes a coronary artery ostium, and the processor is further configured to calculate the measure of blood flow obstruction to the coronary artery ostium based on placement of the digital model of the prosthetic cardiac device within the aortic root.

16. The system of claim 11, wherein the cardiac anatomical structure of the patient-specific digital depiction is a valve annulus of the patient and the adjacent anatomical structure includes a left ventricular outflow tract, and the processor is further configured to calculate the measure of blood flow obstruction through the left ventricular outflow tract based on placement of the digital model of the prosthetic cardiac device within the valve annulus.

17. The system of claim 11, wherein following the virtual placement of the digital model of the prosthetic cardiac device within the cardiac anatomical structure of the patient-specific digital depiction, the processor is further configured to generate a revised patient-specific digital depiction based on computation of a deformation of the cardiac anatomical structure caused by the virtual placement of the digital model of the prosthetic cardiac device, the revised patient-specific digital depiction including an impact of the deformation on the adjacent anatomical structure.

18. The system of claim 17, wherein the processor is configured to compute the deformation of the cardiac anatomical structure using finite element analysis.

19. The system of claim 11, wherein the processor is configured to accept the plurality of digital images of the patient's cardiac anatomy by importing portions of CT-scans of the patient's cardiac anatomy.

20. The system of claim 11, wherein the cardiac anatomical structure comprises a human heart valve and the processor further is configured to generate a patient-specific digital depiction of a valve leaflet of the human heart valve using a plurality of leaflet attachment points.

21. A non-transitory, computer-readable storage medium storing instructions thereon that when executed by one or more processors carries out a method of:
  accepting a plurality of digital images of a patient's cardiac anatomy;
  accessing a digital model of a prosthetic cardiac device;
  generating a patient-specific digital depiction of the patient's cardiac anatomy including a cardiac anatomical structure in fluid communication with an adjacent anatomical structure;
  for a virtual placement of the digital model of the prosthetic cardiac device within the cardiac anatomical structure of the patient-specific digital depiction, calculating a measure of blood flow obstruction to the adjacent anatomical structure of the patient-specific digital depiction resulting from the placement of the digital model of the prosthetic cardiac device; and
  generating information to indicate the measure of blood flow obstruction.

22. The computer-readable storage medium of claim 21, wherein the method carried out by the one or more processors further comprises revising the virtual placement of the digital model of the prosthetic cardiac device responsive to the measure of blood flow obstruction to the adjacent anatomical structure.

23. The computer-readable storage medium of claim 21, wherein the method carried out by the one or more processors further comprises, for a given virtual placement:
  determining a cross-sectional area of the adjacent anatomical structure of the patient-specific digital depiction after placement of the digital model of the prosthetic cardiac device; and
  calculating the measure of blood flow obstruction based on the determined cross-sectional area.

24. The computer-readable storage medium of claim 21, wherein the method carried out by the one or more processors further comprises:
  virtually placing of the digital model of the prosthetic cardiac device within the cardiac anatomical structure of the patient-specific digital depiction by selecting a digital model of a preferred prosthetic cardiac device from amongst a plurality of digital models; and
  calculating, for the digital model of the preferred prosthetic cardiac device, the measure of blood flow obstruction to the adjacent anatomical structure.

25. The computer-readable storage medium of claim 21, wherein the method carried out by the one or more processors further comprises, for a patient-specific digital depiction of the cardiac anatomical structure being an aortic root of the patient and the adjacent anatomical structure being a coronary artery ostium, calculating the measure of obstruction of the blood flow to the coronary artery ostium based on the virtual placement of the digital model of the prosthetic cardiac device within the aortic root.

26. The computer-readable storage medium of claim 21, wherein the method carried out by the one or more processors further comprises, for a patient-specific digital depiction of the cardiac anatomical structure being a valve annulus of the patient and the adjacent anatomical structure being a left ventricular outflow tract, calculating the measure of obstruction of the blood flow through the left ventricular outflow tract based on the virtual placement of the digital model of the prosthetic cardiac device within the valve annulus.

27. The computer-readable storage medium of claim 21, wherein the method carried out by the one or more processors further comprises:
  generating a revised patient-specific digital depiction of the cardiac anatomical structure based on computation of a deformation of the cardiac anatomical structure caused by the virtual placement of the digital model of the prosthetic cardiac device, the revised patient-specific digital depiction including an impact of the deformation on the adjacent anatomical structure.

28. The computer-readable storage medium of claim 27, wherein the method carried out by the one or more processors further comprises computing the deformation of the cardiac anatomical structure using finite element analysis.

29. The computer-readable storage medium of claim 21, wherein the method carried out by the one or more processors further comprises importing portions of CT-scans of the patient's cardiac anatomy.

30. The computer-readable storage medium of claim 21, wherein the method carried out by the one or more processors further comprises, for the cardiac anatomical structure comprising a human heart valve, generating a patient-specific digital depiction of a valve leaflet of the human heart valve using a plurality of leaflet attachment points.

* * * * *